United States Patent
Champeau

(10) Patent No.: US 6,400,976 B1
(45) Date of Patent: Jun. 4, 2002

(54) CATHETER WITH THIN FILM ELECTRODES AND METHOD FOR MAKING SAME

(76) Inventor: Eugene J. Champeau, 505 Alvarado La., Plymouth, MN (US) 55447

( * ) Notice: Subject to any disclaimer, the term of this patent is extended or adjusted under 35 U.S.C. 154(b) by 6 days.

(21) Appl. No.: 09/635,319

(22) Filed: Aug. 9, 2000

Related U.S. Application Data

(63) Continuation of application No. 09/176,009, filed on Oct. 20, 1998.

(51) Int. Cl.$^7$ .................................................. A61N 1/05

(52) U.S. Cl. ........................ 600/374; 607/116; 607/119

(58) Field of Search ................................ 607/116, 119, 607/122; 600/374

(56) References Cited

U.S. PATENT DOCUMENTS 5,470,668 A * 11/1995 Wu et al. .................... 428/688

* cited by examiner

Primary Examiner—Carl Layno
(74) Attorney, Agent, or Firm—Kevin W. Cyr; Rider, Bennett, Egan & Arundel

(57) ABSTRACT

An electrical lead for sensing electrical activity with the body of the patient and for applying electrical energy to selected body tissue comprises an elongated, flexible polymeric lead body having one or more conductors extending the length thereof, the conductors being connected at their distal end to electrode pads where the pads each comprise a multi-layer thin metallic film structure formed on the surface of the lead body where the overall thickness of the composite electrodes are less than about 5 microns. As such, the electrodes do not adversely impact the ability of the distal end portion of the catheter to flex and conform to tissue structures where sensing is to be taken and therapy delivered via the lead.

13 Claims, 4 Drawing Sheets

CATHETER WITH THIN FILM ELECTRODES AND METHOD FOR MAKING SAME

CROSS-REFERENCE TO RELATED APPLICATIONS

This application is a continuation of co(-)pending application Ser. No. 09/176,009, filed Oct. 20, 1998.

BACKGROUND OF THE INVENTION

1. Field of the Invention

This invention relates generally to catheters used in sensing electrical activity within a patient and administering therapy, and more particularly to such catheters incorporating deposited thin film electrodes having improved flexibility and trackability within the body.

2. Discussion of the Related Art

A recognized procedure used in treating various cardiac arrhythmias involves ablating cardiac tissue at an appropriate site to block aberrant re-entrant paths. In a normal heart, the sino-atrial (SA) node located in right atrium depolarizes on a cyclic basis and a resulting electrical wave propagates to the atrio-ventricular (AV) node causing it to fire and send a further electrical wave down the bundle of HIS and there along the left and right bundle branches to produce a coordinated contraction of the ventricles. Arrhythmia, including atrial fibrillation, atrial flutter and tachycardia often results when the heart's normal conduction system includes a re-entrant path from the ventricles to the atrium, resulting in the feedback of electrical impulses that mix with depolarizations of the SA node to deliver erratic signals to the AV node.

In addressing these arrhythmias, procedures referred to as electrophysiology mapping and ablation electrophysiological therapy are used. In carrying out such therapy, a physician will first steer a catheter having sensing/ablation electrodes on the distal end thereof through the patient's vascular system and into a predetermined chamber of the heart where the treatment is to be carried out. The catheter is manipulated so as to place the electrodes into direct contact with the myocardial tissue that is sensed and/or to be ablated. Sensing and/or ablation can be performed on the endocardial surface or via coronary veins and arteries. The aberrant path and/or ectopic foci is first located using a "mapping" technique in which cardiac depolarization signals picked up by the electrodes are transmitted over electrical conductors in the lead to a suitable monitor/analyzer. When an aberrant conductive pathway or an ectopic foci is located, the physician positions the electrodes so that predetermined ones are in direct contact with the myocardial tissue to be ablated. The physician then activates a voltage generator, usually a source of RF voltage connected across a pair of electrodes, to effectively ablate and form a line of scar tissue interrupting the aberrant conductive pathway or to eliminate the ectopic foci.

Those desiring additional information relating to the use of ablation/mapping catheters for treating cardiac arrhythmias are referred to "Catheter Ablation of the Atrioventricular Junction with Radiofrequency Energy" by Landberg et al., *Circulation*, Vol. 80, No. 6, December 1989, "Radiofrequency Catheter Ablation of Atrial Arrhythmias", by Lesh et al., *Circulation*, Vol. 89, No. 3, Mar. 1994, and "Efficacy of Radiofrequency Ablation of Atrial Tissue in Common Atrial Flutter", by Kirkorian et al., *NASPE*, May 1993. The use of electrode carrying catheters for ablating locations within a heart chamber is also disclosed in U.S. Pat. Nos. 4,641,649; 4,892,102; and 5,025,786.

The related art further discloses a number of different electrode configurations. In the Fleischhacker et al. U.S. Pat. No. 5,676,662, a conductive wire helix is wrapped about an elongated polymer catheter body where certain portions of the turns of the helix are uncoated so as to expose bare metal that forms the electrode surfaces. In the Swanson et al. U.S. Pat. No. 5,582,609 discrete helical windings are disposed near the distal end of an elongated flexible plastic catheter. The helical winding is intended to provide increased flexibility for allowing the catheter to better conform to the surface of the tissue to be ablated. In the Pomeranz et al. U.S. Pat. No. 5,558,073, the electrodes each comprise a metallic ring disposed about the circumference of the catheter body. A plurality of electrical conductors extend through a lumen of the catheter body to connect the metallic rings to terminals at the proximal end of the catheter body. Such ring electrodes are also shown in the Truckai et al. U.S. Pat. No. 5,487,757. In the related art arrangements, the ring electrodes are typically preformed bands of metal that are adhesively bonded, crimped or otherwise attached to the exterior surface of the catheter body, and which are connected by electrical conductors that extend through one or more lumens in the catheter body to connectors at its proximal end. These rings tend to be relatively thick and are therefore rigid. When it is considered that up to ten such ring electrodes are typically spaced about one centimeter apart along the distal end portion of the catheter body, they impact the ability of the distal end portion of the catheter to flex and conform to tissue structures to be mapped/ablated.

Leads constructed in accordance with the present invention can find use not only in mapping the endocardium and ablating tissue to treat cardiac arrhythmias, but also can be used in fabricating pacing and defibrillating leads as well as neurological leads placed along the spinal column by which electrical stimulation can be applied to the body for treating chronic pain.

It is a principal purpose of the present invention to provide an improved electrophysiology catheter that exhibits improved flexibility when contrasted with known related art mapping and ablation catheters. Rather than using a plurality of solid, preformed, tubular, metal ring electrodes, we instead deposit multiple layers of different metals as thin films so that the resulting multi-layer structure may have a thickness between 5 and 250 microns, but with between 5 and 20 microns being preferred. With such thin electrodes, they are able to readily flex and do not detract from the overall flexibility of the distal end portion of the catheter. Moreover, they can be configured in various shapes and patterns to optimize tissue contact.

Historically, thin metallic films have not been suitable for use as conductive electrodes on flexible polymers, although efforts to do so have been attempted. Past efforts have been plagued with a number of problems including: (1) being able to adhere the thin metal film coating to the polymer substrate, especially on flexure thereof; (2) lack of adhesion of the coating to itself (internal adhesion) as the coating is oxidized by air; (3) formation of cracks emanating in the film which lead to either loss of conductivity or undesirable "spark gaps"; (4) temperature build-up in the film resulting from internal micro-cracks which overwhelm the minimal heat capacity of a metal that is less than 1 mil thick; and (5) inherent stresses that exist in a columnar structured film as it is longitudinally stretched. Because of the aforementioned problems, persons skilled in the art of designing and producing electrical leads/catheters have stayed away from the use of thin films even though such thin film electrodes offer significant advantages, especially enhanced flexibility and improved configuration to optimize contact along an interior surface of a body cavity, and greater energy transfer because such films have no thermal capacity and, hence, no heating occurs of the film itself. As such, there is no loss of energy in the thermal heating of the thin film ring electrode.

SUMMARY OF THE INVENTION

The present invention provides a method for creating a thin metallic film electrode structure for use on electrical leads that may be used for detecting electrical activity within the body of a patient and for administering therapy. Using the method of the present invention, electrically conductive thin film coatings can comprise electrodes on mapping and/or ablation catheters or other electro-physiologic catheters without incurring the aforementioned problems and because of the thin structure of the multi-layer electrodes they readily flex without destroying the integrity of the electrode, allowing the electrodes to conform to the surface where mapping and/or ablation is to occur.

In broad terms, the invention comprises an electrical lead having an elongated, flexible, polymer lead body with a proximal end, a distal end and supporting at least one conductor extending from the proximal end to a predetermined zone located proximate the distal end of the lead body. At least one electrode is formed on the exterior surface of the lead body in that zone, the electrode being a conductive pad comprising a plurality of superimposed thin metallic film layers. The electrode can be applied to the lead body in a variety of configurations, including concentric bands, elongated, linear bands, discrete spots, etc. The electrode may, for example, have a composite thickness less than about 5 microns. Means are provided for connecting the thin film electrode to the conductor, whereby cardiac depolarization (EKG) signals or other nerve impulses picked up by the electrodes may be conveyed to an analyzer and RF voltages for administering therapy may be applied between a pair of such electrodes on the lead body, in the case of a bipolar lead, or between an electrode on the lead and a body plate or other return electrode where a monopolar lead is being used.

Without limitation, the first thin metal layer on the polymer substrate may be titanium, chromium, aluminum or nickel and the thickness of this first layer may typically be less than about 5 microns in thickness. To enhance adherence of this coating to the polymer substrate, the coating is either concurrently bombarded during its deposition by high energy ions, which serve to "shot-peen" the film layer into the surface of the polymer and to continuously break up the coating from an amorphous/columnar structure to a nanocrystalline structure, exhibiting over-lapping platelet regions. As used herein, the term "nanocrystalline" means that the metal layer is comprised of many, many minute plate-like structures (crystals). The concurrent bombardment is commonly referred to by the acronym "IBAD" for ion beam assisted deposition. Alternatively, so-called ion beam enhanced deposition or "IBED" may be used where ion beam bombardment is applied subsequent to the deposition of the metallic layer.

A second thin metal film layer or coating is subsequently deposited over the first layer and when formed of palladium or platinum of a thickness less than 1,000 angstroms, functions as a self-alloying/oxygen diffusion barrier layer. Again, the deposition preferably takes place in the presence of high energy ions to enhance interlacing between the base layer and the second layer, again providing a desired stress-free and non-columnar structure.

A third metal film layer is then applied to a predetermined thickness to function as a bulk conductive layer. It comprises platinum or silver or a similar conductive element or alloy and nominally lies in a range of between 500 angstroms and 50 microns in thickness, but with 0.5 to 5.0 microns being a preferred range. It is found that a third layer of about 2.0 to 3.0 microns in thickness is sufficient to meet the skin depths required for the RF electrical signal employed for ablation but that an upper limit of 250 microns still allows the catheter to possess a desired flexibility.

Finally, a fourth deposited thin metal film layer is applied over the third layer to act as a biocompatible, conductive layer. While various metals may be used, gold is preferred. Gold is a soft metal exhibiting very low stress. The fourth layer is nominally less than 1,000 angstroms in thickness, but may be in a range of from 500 angstroms to 50 microns.

BRIEF DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DETAILED DESCRIPTION OF THE INVENTION

Figure 1:
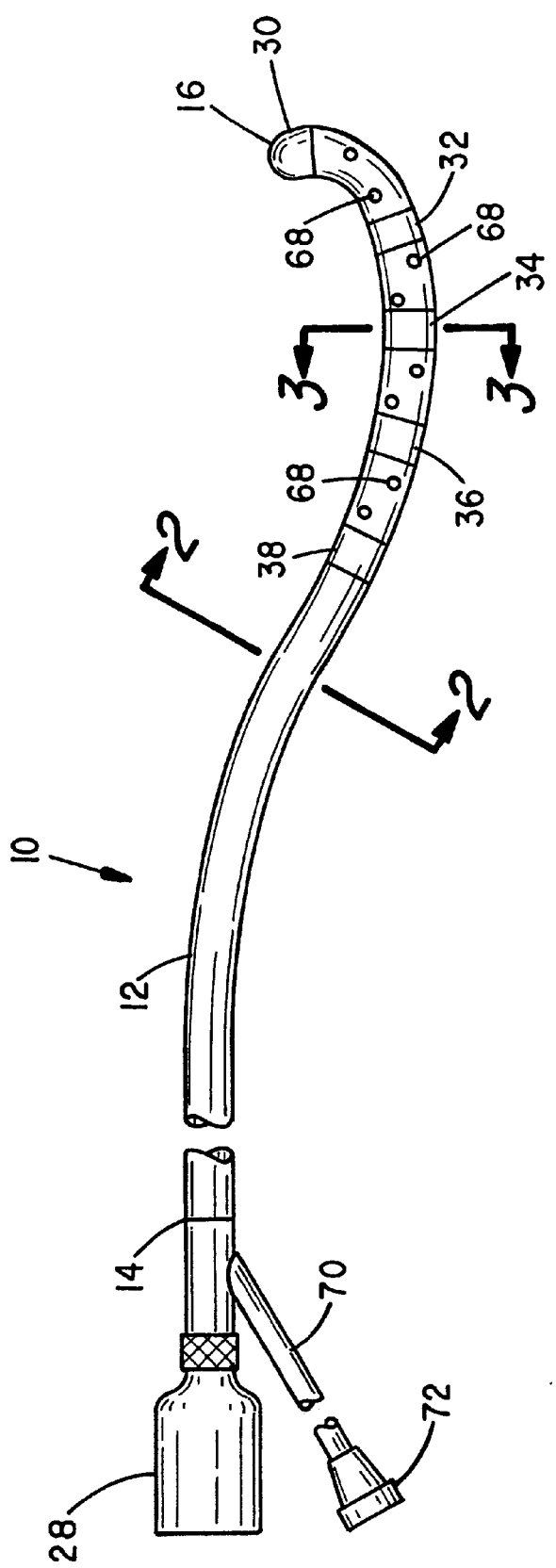
FIG. 1 is an enlarged perspective view of a mapping/ablation lead constructed in accordance with the present invention.

Referring first to FIG. 1, there is indicated generally by numeral 10 an electro-physiologic lead constructed in accordance with the present invention. Without limitation, the lead 10 may be designed for use in cardiology for mapping a patient's cardiac chamber to locate aberrant re-entrant paths and ectopic foci and for subsequently ablating tissue in the treatment of certain cardiac arrhythmias. Alternatively, the lead can be designed for neurologic use, such as for intracranial mapping, deep brain stimulation or placement in the intrathecal space surrounding the spinal chord for administering electrical stimulating impulses in the treatment of chronic pain. Other uses may include electrical leads for use with external or implantable pulse generators and/or defibrillators.

The catheter or lead 10 includes an elongated, highly flexible polymeric lead body 12 having a proximal end 14 and a distal end 16. The lead body 12 may be extruded from a variety of different polymers, depending upon the particular application, such as fluorinated ethylene propylene (FEP), polyethylene, silicone rubber, polyurethane, polyamide, polyimide, polytetrafluoroethylene (PTFE), and polyvinylchloride (PVC). Moreover, alloys of these materials as well as blends thereof may also be formulated in known manners to control the relative flexibility, torqueability, and pushability.

Figure 2:
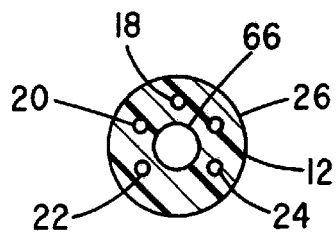
FIG. 2 is a greatly enlarged cross-sectional view taken along the line 2—2 in FIG. 1.

As is shown in FIG. 2, the lead body 12 may be co-extruded with one or more micro-helical wires as at 18, 20, 22, 24, and 26 embedded therein. These conductors may comprise multifilar conductors made of MP35 stainless steel, platinum, platinum-iridium or copper and they extend from a proximally located electrical connector 28 to a corresponding plurality of electrodes 30, 32, 34, 36 and 38 disposed in a zone proximate the distal end 16 of the catheter body 12. While the view of FIG. 2 shows the conductors 18–26 embedded in the polymer comprising the lead body 12, it is also contemplated that the conductors may be fine ribbons that are affixed to and spiral along the outer surface of the lead body 12 where they make connection individually to the aforementioned electrodes. Suitable materials for the ribbon conductors include Al, Ag, Au, Pd, Ti, Cr, Ni, Pt, Pt—Ir, Cu, alumel, chromel, constantin and alloys thereof. When surface conductors are employed, they would be covered by an insulative coating except where they join to the distal electrodes.

Again, depending upon the particular application, the diameter of the lead body may be as small as from 2 to 3 French for neurological and myocardial mapping/ablation leads and up to about 8 to 12 French for other applications.

Figure 3:
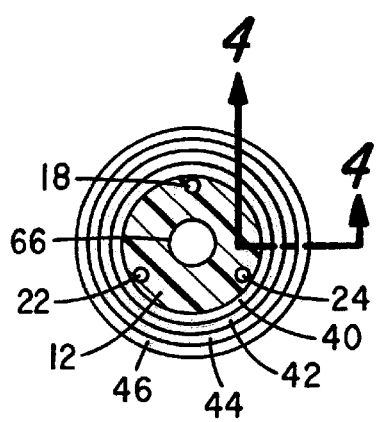
FIG. 3 is a greatly enlarged, not-to-scale, cross-sectional view taken along the line 3—3 in FIG. 1.
Figure 4:
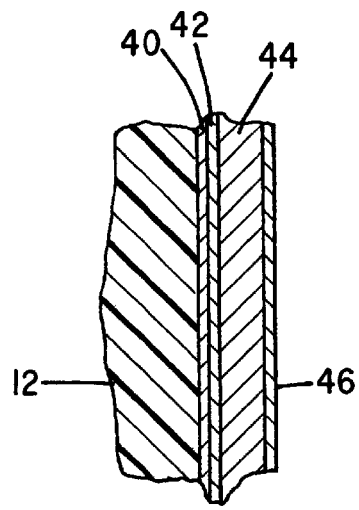
FIG. 4 is a greatly enlarged, not-to-scale, cross-sectional view taken along the line 4—4 in FIG. 3.

In accordance with the present invention, the electrodes 30–38 comprise a multi-layer structure of thin metal films that are sequentially deposited through an appropriate mask arrangement onto the exterior surface of the lead body. With reference to FIGS. 3 and 4, a first layer of metal 40 is deposited directly on the lead body 12 to a thickness less than about 5 microns. This innermost layer may preferably be titanium, chromium, aluminum or nickel. As will be explained more fully below when the details of the method of manufacture are set forth, the deposition of this layer is performed while the polymer substrate and the metal being deposited are bombarded with high energy ions (IBAD). It is found that the deposition in the presence of the bombarding ions effectively shot peens the film into the polymer to enhance the adhesion of the inner layer 40 as it is being formed to the polymer substrate. In addition, the impact of the high-energy ions tends to continuously break up the metal coating from an amorphous, columnar structure to a more crystalline structure exhibiting overlapping planar regions. An IBED process may be used as well.

Once the film 40 has condensed and solidified on the substrate, a second layer 42 is vapor deposited as high-energy ions again are allowed to bombard the target area where the electrodes are being formed. The second layer 42 adjacent the innermost layer 40 again may have a thickness between 500 angstroms and 50 microns and preferably comprises palladium or platinum. It functions as a self-alloying oxygen diffusion barrier layer which prevents oxides from forming on the surface of the adhesion layer which would prevent prior adhesion of subsequently deposited layers and which would act as an electrical insulator. The high-energy ions enhance interlacing between the base layer 40 and the second layer 42 while again providing a desired stress-free and non-columnar structure.

Following deposition of the layer 42, the deposition process, either IBAD or IBED, is repeated for a further layer 44. Layer 44 is substantially thicker than layers 40 and 42 so as to act as a bulk conductive layer. The layer 44 may comprise platinum, silver, gold or copper, which are good thermal conductors. The third film layer may typically be from about 2 to 250 microns in thickness. The metal layer 44 is deposited in the same manner as the first two coatings, but in this case, the goal is to have a sufficient thickness needed to meet the skin depths required for the particular electrical signal to be employed. While lower thicknesses can be achieved to meet the needs of mapping in a cardiac chamber, or for DC transmission when RF energy is to be applied for ablation, the thicker coatings are required.

Finally, an outer layer 46 can be vapor deposited in the presence of high energy ions that are made to bombard the target area either during or subsequent to the metal deposition. The fourth and outer layer is deposited to act as a biocompatible and conductive layer. It can consist of a variety of metals, with gold and platinum being preferred because they are conductive, flexible, and exhibit very low internal stress when applied with this process. The outer layer 46 may be deposited to a thickness of between 500 Å and 50 microns. Where the application may require passage of the catheter several times through introducers or guide catheters, the outer coating may comprise PtIr which is generally harder and more abrasion-resistant than gold. In either event, the film needs to have high emissivity, good thermal characteristics, and conductivity properties to ensure that no thermal mismatches occur within the composite layered film electrodes.

In summary and without limitation, the preferred embodiment of the invention may consist of a inner film layer of titanium about 1000 angstroms thick, a second layer of palladium about 1000 angstroms thick, a third layer of silver about 5 microns thick, and a fourth, covering layer of gold. The composite film possesses in sufficient thickness to be above the required skin depth for the electrode which nominally is about 0.2 microns for a 500 kHz RF signal. The resulting electrode has excellent adhesion to the underlying polymeric lead body and little or no internal stress so there is no cracking in the film layers as the lead body is stretched. With no cracking, problems in the related art associated with "spark gaps" across such cracks and resistive heating are obviated.

Figure 5:
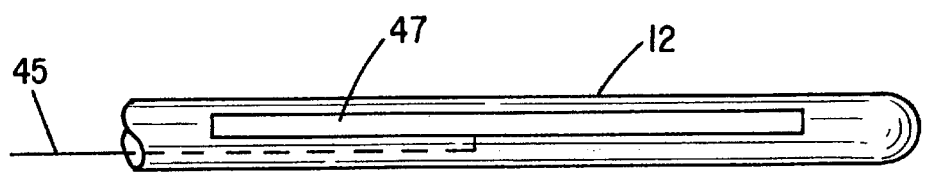
FIG. 5 is a partial view of a catheter with an elongated linear electrode on a surface thereof.

FIG. 5 is a partial view of a mapping/ablation lead on which is deposited a multi-layer thin metallic film electrode 47 of the type described. It is relatively long and linear. A conductor 45 extends through the polymer catheter body 12 for applying electrical energy to the electrode. Using this electrode configuration allows ablation over an elongated area on the surface of the myocardium without the need to drag the electrode over the myocardial tissue.

Figure 6:
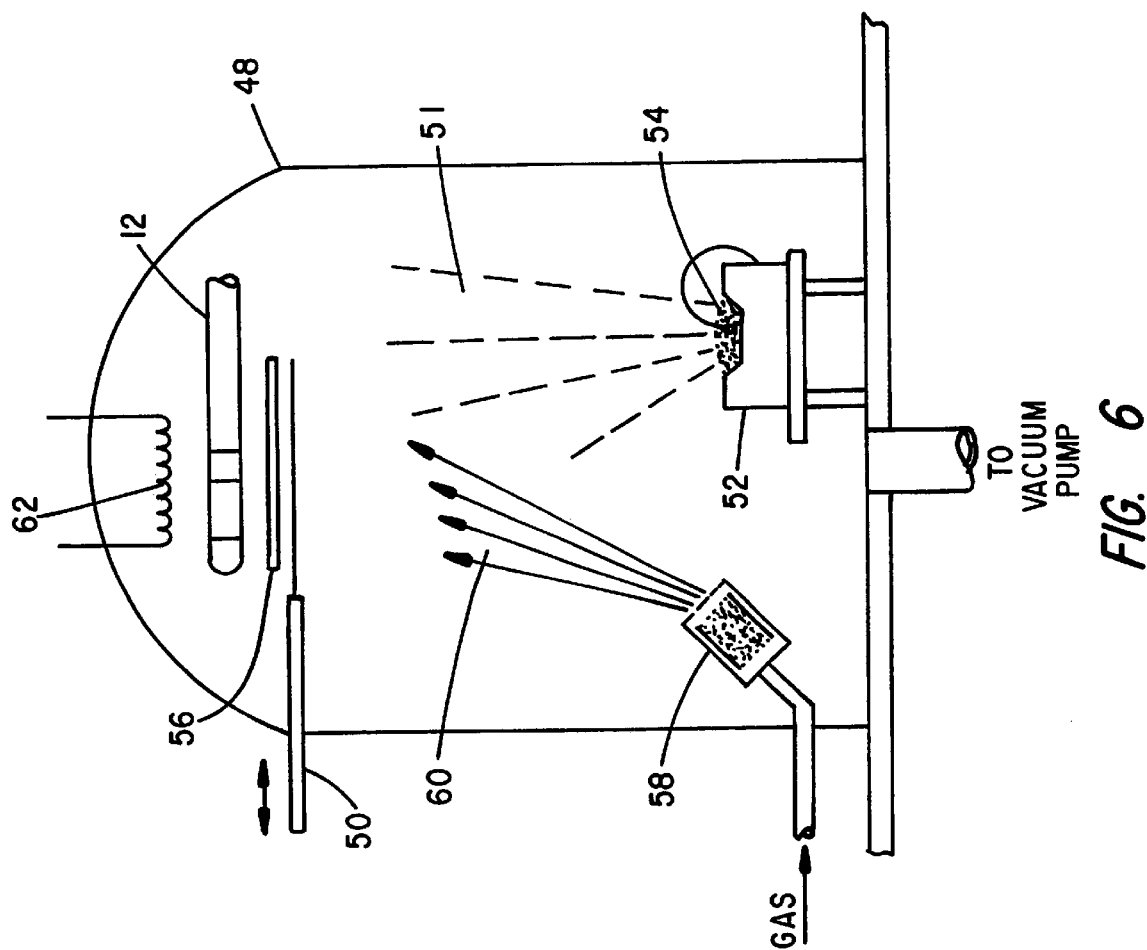
FIG. 6 is a schematic drawing of an apparatus that may be used in fabricating the multi-layer thin film electrodes of the present invention.

FIG. 6 schematically illustrates one apparatus whereby electrical leads, having multi-layer thin metal film electrodes, can be produced. Numeral 48 comprises a vacuum chamber, the interior of which can be pumped down to a pressure of about $10^{-7}$ Torr. Disposed within the chamber is a shutter 50 that can be manipulated from outside of the chamber to expose the distal end portion of the catheter body 12 to metal evaporant 50 emanating from a boat 52 containing the metal material 54 to be deposited. The metal material 54 may be vaporized by thermal heating of the boat 52 or by electron beam sputtering, all as is well known in the semiconductor processing arts. A mask, as at 56, is used to define the length of and spacing between the individual film electrodes as they are being formed on the lead body.

Also contained within the vacuum chamber 48 is an ion gun 58 for directing an ion beam 60 through the mask and onto the target when the shutter 50 is open. The ions are produced by injecting a gas, such as argon, nitrogen or oxygen through a screen maintained at high voltage. Those skilled in the art of thin film deposition techniques will recognize that the apparatus of FIG. 6 would also typically include biasing and focusing electrodes controlling the bombardment of the film layers during their deposition. To thermally relieve any stresses that might otherwise develop in the thin film electrodes as they are being formed, a radiant heater, as at 62, may be provided as well.

Figure 7:
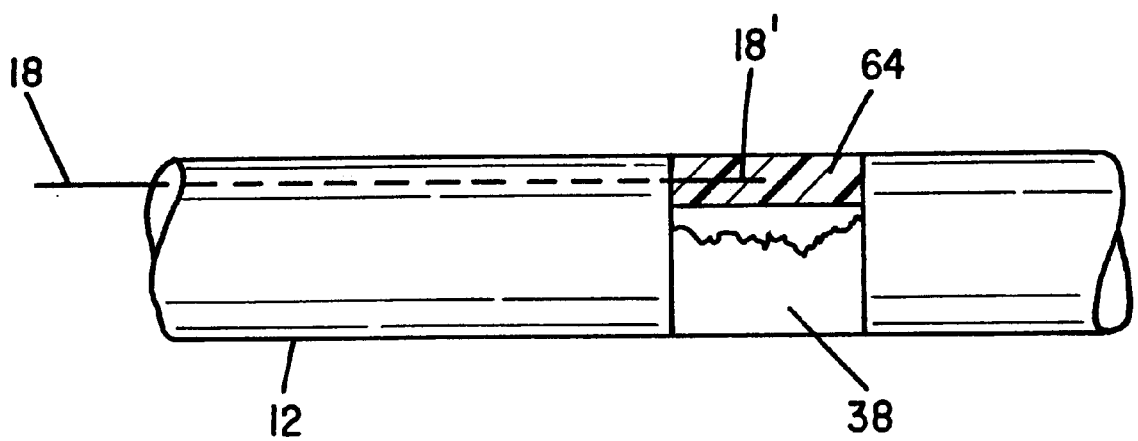
FIG. 7 is a greatly enlarged, partially cut-away view of a catheter body showing one technique for connecting an elongated conductor in the lead to a thin film electrode.

While the apparatus of FIG. 6 illustrates only one boat 52 containing a metal to be vaporized, it can be readily understood that additional boats, each with its own particular metal, may be contained within the evacuated chamber 48 and sequentially heated to vaporize its contents in forming the multiple layers comprising the electrode without having to break the vacuum. Vapor deposition with ion-beam bombardment is a preferred method of forming the multilayer, thin film electrodes. The several metals comprising the layers can be evaporated using any of e-beam impingement, thermal (resistive) heating, RF sputtering or plasma sputtering In FIG. 7, there is shown a greatly enlarged, partially sectioned view of the catheter body 12 showing one way in which an electrical connection can be made between the film electrode 38 and a conductor 18. Here, the catheter body is first prepared by cutting away a portion of the polymer comprising the catheter body to thereby expose a distal end portion 18' of the conductor 18. Laser cutting of the polymer is preferred, but grinding or even chemical removal of the polymeric material can be employed. The recess formed in the catheter body 12 is then back-filled with a conductive material, such as conductive epoxy 64, until it is again flush with the outside surface of the catheter body 12. Now, when the base metal film layer 40 on electrode 38 is vacuum deposited onto the lead body in the manner described above, electrical contact will be made between it and the conductive back-filling material and, thence, to the conductor 18 leading to a terminal connector 28 on the proximal end of the lead body. Other methods of connecting either embedded conductors or surface ribbon conductors to the thin film electrodes include soldering, crimping a suitable connector to both the electrode and the elongated conductor. A further approach for providing an interconnection between the elongated conductor and the film electrode involves melting the conductor wires into the wall of the catheter body and subsequently scraping away any covering layer of plastic to thereby provide a metallic surface unto which the base film layer of the electrode can be directly applied. Once the base layer is in place, the oxide barrier layer, the conductive layer and the outer biocompatible layer can be sequentially deposited.

While FIGS. 1 and 3 show the multi-layer thin metal film electrodes as continuous bands or toroids, other patterns, such as split rings, spot or strip electrodes may be used as well by providing an appropriate mask arrangement during the vacuum deposition process or by post-deposition laser etching. Such masking techniques include the use of tape, preferably Kapton® manufactured by Dupont High Performance Films, Inc. in Circleville, Ohio, heat shrink tubing, metal shields, a polymeric sleeve. Irrespective of the masking technique employed, it is desirable to have electrode pads with sharp rather than tapered edges. It is found that when frequency RF energy is applied to thin film electrodes having irregular or tapered edges, non-uniform tissue burning results and there is propagation of heat along the edges of the film. Again, without limitation, the thin film electrodes may range in length from about 1 cm to 10 cm, depending upon the application for which the lead/catheter is being designed. Even with a continuous band that is 10 cm in length, because the electrodes are so thin, flexibility is not sacrificed.

With a lead/catheter designed for RF ablation, it may be desirable to provide cooling of the electrodes to keep the surface temperature below 100° C., but above 48° C. Referring to FIGS. 1–3, such cooling can be achieved by providing at least one lumen 66 that extends between the proximal end 14 and the distal end 16 of the catheter. A plurality of apertures or bores 68 are formed through the wall of the tubular catheter body 12 to intersect the lumen 66. The proximal connector 28 also includes a flushing port 70 that is in fluid communication with the lumen 66, allowing cooled saline solution to be injected through the Luer fitting 72 and the injection port 70 and flow through the lumen 66 to exit the catheter at the distal end portion thereof by way of the apertures 68. In this way, the chilled saline can be made to bathe the electrodes. With multiple electrodes, the catheter body 12 may be designed to have a plurality of lumens so that cooling fluid can be injected selectively to those particular electrode pads that may require cooling. By controlling the saline injection rate, i.e., as by activating when the electrode temperature arises above a predetermined threshold and deactivating when it falls below that threshold, one can achieve a better and deeper heat penetration profile without over-heating beneath the tissue surface. Temperature sensing and regulation may be achieved by using a thermistor material, such as constantin, alumel, or chromel, that are also good conductors as the layer 44 in the multi-layer film, the same conductor wire connected to the thin film electrode can be switched between a RF source for ablating and a DC source for temperature sensing. Alternatively, a thermistor device may be disposed within the tip of the catheter body as a discrete element rather than being incorporated into the film electrode itself. In either event, with a microprocessor-based control system, the sensing may comprise a feedback loop for regulating the RF power level to a desired set point temperature, obviating the need for irrigation. Those skilled in the art will also recognize that the catheter body stock 12 may be designed to have an inherent memory property whereby the distal end portion will assume a predetermined shape configuration when in a free state, i.e., without any external forces acting on same. Because of the relative thinness of the composite multi-layer electrode structures, the distal end portion can be sufficiently supple to conform to tissue structures to be ablated.

To study the effects of time and power on the ability of the thin film coating to burn canine cardiac tissue without self-destructing, we coated seven different polymeric substrates with a multi-layer thin film electrode comprised of one configuration which was one of the preferred coating compositions. Canine heart tissue was used in the experiment. Tests were conducted using an RF generator (Valleylab Model SSE2L Electrosurgical Instrument) operated in the unipolar mode. Power settings of 25, 50 and 75 watts were used at a frequency of 500 MHz. Current settings of 25, 50 and 75 watts were used at a frequency of 500 MHz. Current was applied to each electrode sample in 15, 30 or 45 second intervals. This was performed with and without irrigation of the tissue with saline. The tissue damage and lesion depth was measured for each sample.

Even at low and mid level power settings, some of the electrodes created non-uniform burns. This appeared to be very dependent on the polymeric substrate material. On several polymeric substrates, the electrode was able to burn tissue without signs of degradation at all power levels. Irrigation was performed at higher power levels which increased burn depth, created more uniform burns with reduced charring without electrode damage. Burn depths ranged from 2–9 mm and increased substantially with irrigation. We concluded that the thin film electrode of the present invention is capable of delivering RF energy on selected substrate materials resulting in good bum depth with and without irrigation and without electrode destruction.

While in the above study, tissue ablation was effected by operating in a monopolar mode using a remote return electrode, it is contemplated that an RF voltage may be applied between a selected pair of electrodes on the lead itself in a bipolar mode.

The invention has been described herein in considerable detail in order to provide those skilled in the art with information needed to apply the novel principles disclosed. However, one skilled in the art will appreciate that many different configurations and shapes of the electrode as well as the lead described herein are possible. Further, it should be understood that the invention can be carried out by other different equipment and processes, and that the various modifications, both as to physical details and operating functions can be effected without departing from the scope of the invention itself. The description herein is intended by way of example only, and is not intended to limit the invention, except as set forth in the following claims.

What is claimed is:

1. A medical lead, comprising:
   a lead body including at least one conductor, the lead body having an outer surface; and
   at least one electrode attached to the outer surface, the electrode comprising a plurality of adjacent metallic film layers, at least two adjacent metallic film layers bonded by electron bombardment.

2. A lead, as in claim 1, wherein an innermost metallic film layer is a metal selected from a group consisting of Ti, Cr, Ni, and Al.

3. A lead, as in claim 2, wherein the metallic film layer adjacent the innermost metallic film layer is a metal selected from a group consisting of Pd and Pt.

4. A lead, as in claim 1 wherein an outermost metallic film layer is a metal selected from a group consisting of Au, Pt and Pt—Ir.

5. A lead, as in claim 4, wherein a metallic film layer adjacent the outermost metallic film layer is a metal selected from a group consisting of Ag, Pt, Cu and Au.

6. A lead, as in claim 1, wherein the lead body has an outside diameter in a range of from about 2 F to about 11.5 F.

7. A method of manufacturing medical leads, comprising:
   providing a lead body including at least one conductor, the lead body having an outer surface;
   depositing a plurality of metallic film layers, at least two of the metallic film layers adjacent to one another; and
   bombarding the metallic film layers with accelerated ions to bond at least two of the adjacent metallic film layers.

8. A method, as in claim 7, further comprising masking the lead body to form a plurality of discrete areas on the lead body on which the metal film layers are formed.

9. A method, as in claim 7, wherein at least one of the metallic film layers has a thickness between 500 angstroms and 1 micron.

10. The method as in claim 7, wherein at least one of the metallic film layer has a thickness less than about 250 microns.

11. A method, as in claim 7, wherein at least one metallic film layer is a metal selected from a group consisting of Ag, Al, Au, Cr, Cu, Ni, Pd, Pt, Pt—Ir and Ti.

12. A method, as in claim 7, wherein the lead body is a polymer selected from a group consisting of PTFE, PET, PVC, PFA, e-PTEB, polyethylene, silicone rubber, polyurethane, polyamide, polyimide and FEP.

13. A method, as in claim 7, wherein the bombarding ions are selected from a group consisting of Ar, N, and O.

* * * * *